United States Patent [19]

Chuang et al.

[11] Patent Number: 6,083,734
[45] Date of Patent: Jul. 4, 2000

[54] RECOMBINANT XYLANASE, THE PREPARATION AND USE OF THEREOF

[75] Inventors: Ming-Hon Chuang; King-Song Jeng; Shaw-Yun Wu; Lung-Shen Lin; Edward L. Chang, all of Taipei, Taiwan

[73] Assignee: Development Center for Biotechnology, Taipei, Taiwan

[21] Appl. No.: 09/260,283

[22] Filed: Mar. 2, 1999

[30] Foreign Application Priority Data

Mar. 6, 1998 [TW] Taiwan ................................. 87103297

[51] Int. Cl.[7] ...................................................... C12N 9/24
[52] U.S. Cl. ...................... 435/200; 435/69.1; 435/252.3; 435/254.2; 435/320.1; 536/23.1; 536/23.2; 536/23.7
[58] Field of Search ...................................... 435/200, 69.1, 435/252.3, 254.2, 320.1; 536/23.2, 23.4, 23.7, 23.1, 24.33

Primary Examiner—Rebecca Prouty
Assistant Examiner—Richard Hutson
Attorney, Agent, or Firm—Ladas & Parry

[57] ABSTRACT

The present invention provides a genetically recombinant xylanase with high yield and good activity, and a process for the production of the recombinant xylanase. The present invention also provides the coding sequence of the recombinant sequence, vectors bearing the coding sequence and the transformants containing the vectors. The present invention further provide a column wherein the recombinant xylanase is immobilized.

12 Claims, 12 Drawing Sheets

```
Nde I                                              49
CATATGAATGCCCAAACCCTGAGTTCAAATTCAACGGGTACCAATAACG
                                                   98
GTTTTACTACACCTTCTGGAAAGATTCCGGTGATGCGTCCATGACGTT
                                                  147
ATTGTCTGGCGGTCGTTACCAATCATCCTGGGGCAACTCCACCAATAAC
                                                  196
TGGGTGGGTGGTAAAGGCTGGAATCCTGGTAATAATTCGCGGGTTATCA
                                                  245
GCTATTCCGGTTCTTACGGTGTTGATAGCAGCCAAAATTCCTACCTGGC
                                                  294
GCTCTATGGCTGGACCCGGAGTCCGCTGATCGAATACTACGTGATTGAA
                                                  343
AGTTACGGTTCCTACAACCCGGCCAGCTGCTCCGGCGGCACTGACTACG
                                                  392
GCAGCTTCCAGAGTGATGGTGCCACCTATAACGTGCGTCGCTGCCAGCG
                                                  441
CGTTAACCAACCCTCGATTGATGGTACCCAAACCTTCTACCAATACTTC
                                                  490
AGTGTCAGGAATCCGAAAAAAGGGTTCGGCAACATCTCCGGTACCATT
                                                  539
ACCTTTGCCAACCACGTTAATTTCTGGGCGAGCAAGGGTTTGAATTTGG
                                                  588
GTAACCACAATTATCAGGTACTGGCGACCGAGGGTTACCAAAGCCGTGG
                                                  637
CAGTTCCGACATTACCGTTAGCGAATCAAGCTCCGGTGGCAGCAGCAGT
                                                  686
GTCGCGCTCAGTAGCAGCAGTCGTAGCAGTAGCAGTGCGGGCGGTAATA
                                                  735
CCGGCGGCAATTGCCAATGCAATTGGTGGGGACTTTCTATCCGCTTTG
                                                  784
CCAAACCCAGACCAGTGGTTGGGGCTGGGAAAATTCGCGCAGCTGTATC
                                                  833
AGTACCAGTACCTGTAACAGCCAGGGGACTGGCGGCGGCGGTGTCGTTT
     841
GTAATTGACTCGAG
         XhoI
```

FIG.3

MNAQTLSSNS[010] TGTNNGFYYT[020] FWKDSGDASM[030] TLSSGGRYQS[040]

SWGNSTNNWV[050] GGKGWNPGNN[060] SRVISYSGSY[070] GVDSSQNSYL[080]

ALYGWTRSPL[090] IEYYVIESYG[100] SYNPASCSGG[110] TDYGSFQSDG[120]

ATYNVRRCQR[130] VNQPSIDGTQ[140] TFYQYFSVRN[150] PKKGFGNISG[160]

TITFANHVNF[170] WASKGLNLGN[180] HNYQVLATEG[190] YQSRGSSDIT[200]

VSESSSGGSS[210] SVALSSSSRS[220] SSSAGGNTGG[230] NCQCNWWGTF[240]

YPLCQTQTSG[250] WGWENSRSCI[260] STSTCNSQGT[270] GGGGVVCN[278]

FIG.4

SEQUENCE LISTING

```
<160> NUMBER OF SEQ ID NOS: 8

<210> SEQ ID NO 1
<211> LENGTH: 847
<212> TYPE: DNA
<213> ORGANISM: Artificial Sequence
<220> FEATURE:
<221> NAME/KEY: unsure
<222> LOCATION: (1)
<223> OTHER INFORMATION: Recombinant xylanase gene xyld1
<220> FEATURE:
<223> OTHER INFORMATION: Description of Artificial Sequence: Primer
      sequence for amplifying xylanase genes

<400> SEQUENCE: 1
catatgaatg cccaaaccct gagttcaaat tcaacgggta ccaataacgg tttttactac     60
accttctgga aagattccgg tgatgcgtcc atgacgttat tgtctggcgg tcgttaccaa    120
tcatcctggg gcaactccac caataactgg gtgggtggta aaggctggaa tcctggtaat    180
aattcgcggg ttatcagcta ttccggttct tacggtgttg atagcagcca aaattcctac    240
ctggcgctct atggctggac ccggagtccg ctgatcgaat actacgtgat tgaaagttac    300
ggttcctaca acccggccag ctgctccggc ggcactgact acggcagctt ccagagtgat    360
```

```
ggtgccacct ataacgtgcg tcgctgccag cgcgttaacc aaccctcgat tgatggtacc    420
caaaccttct accaatactt cagtgtcagg aatccgaaaa aaagggttcg gcaacatctc    480
cggtaccatt acctttgcca accacgttaa tttctgggcg agcaagggtt tgaatttggg    540
taaccacaat tatcaggtac tggcgaccga gggttaccaa agccgtggca gttccgacat    600
taccgttagc gaatcaagct ccggtggcag cagcagtgtc gcgctcagta gcagcagtcg    660
tagcagtagc agtgcgggcg gtaataccgg cggcaattgc caatgcaatt ggtgggggac    720
tttctatccg ctttgccaaa cccagaccag tggttgcggc tgggaaaatt cgcgcagctg    780
tatcagtacc agtacctgta acagccaggg gactggcggc ggcggtgtcg tttgtaattg    840
actcgag                                                              847
```

<210> SEQ ID NO 2
<211> LENGTH: 278
<212> TYPE: PRT
<213> ORGANISM: Artificial Sequence
<220> FEATURE:
<223> OTHER INFORMATION: Description of Artificial Sequence: Amino acid
      sequence encoded by the recombinant xylanase gene
      xyld 1

<400> SEQUENCE: 2

```
Met Asn Ala Gln Thr Leu Ser Ser Asn Ser Thr Gly Thr Asn Asn Gly
 1               5                  10                  15

Phe Tyr Tyr Thr Phe Trp Lys Asp Ser Gly Asp Ala Ser Met Thr Leu
            20                  25                  30

Ser Ser Gly Gly Arg Tyr Gln Ser Ser Trp Gly Asn Ser Thr Asn Asn
        35                  40                  45

Trp Val Gly Gly Lys Gly Trp Asn Pro Gly Asn Asn Ser Arg Val Ile
    50                  55                  60

Ser Tyr Ser Gly Ser Tyr Gly Val Asp Ser Gln Asn Ser Tyr Leu
65                  70                  75                  80

Ala Leu Tyr Gly Trp Thr Arg Ser Pro Leu Ile Glu Tyr Tyr Val Ile
                85                  90                  95

Glu Ser Tyr Gly Ser Tyr Asn Pro Ala Ser Cys Ser Gly Gly Thr Asp
            100                 105                 110

Tyr Gly Ser Phe Gln Ser Asp Gly Ala Thr Tyr Asn Val Arg Arg Cys
        115                 120                 125

Gln Arg Val Asn Gln Pro Ser Ile Asp Gly Thr Gln Thr Phe Tyr Gln
    130                 135                 140

Tyr Phe Ser Val Arg Asn Pro Lys Lys Gly Phe Gly Asn Ile Ser Gly
145                 150                 155                 160

Thr Ile Thr Phe Ala Asn His Val Asn Phe Trp Ala Ser Lys Gly Leu
                165                 170                 175

Asn Leu Gly Asn Gly Asn Tyr Gln Val Leu Ala Thr Glu Gly Tyr Gln
            180                 185                 190

Ser Arg Gly Ser Ser Asp Ile Thr Val Ser Glu Ser Ser Gly Gly
        195                 200                 205

Ser Ser Ser Val Ala Leu Ser Ser Ser Arg Ser Ser Ser Ala
    210                 215                 220

Gly Gly Asn Thr Gly Gly Asn Cys Gln Cys Asn Trp Trp Gly Thr Phe
225                 230                 235                 240

Tyr Pro Leu Cys Gln Thr Gln Ser Gly Trp Gly Trp Glu Asn Ser
                245                 250                 255
```

-continued

```
Arg Ser Cys Ile Ser Thr Ser Thr Cys Asn Ser Gln Gly Thr Gly Gly
        260                 265                 270

Gly Gly Val Val Cys Asn
        275
```

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer
      sequence for amplifying xylanase genes

<400> SEQUENCE: 3
attaccgtta gcgaatcaag ctccggtggc agcagc                    36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Primer
      sequence for amplifying xylanase gene

<400> SEQUENCE: 4
gccaccggag cttgattcgc taacggtaat gtcgga                    36

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Primer
      sequence containing NdeI recognition sequence for
      amplifying xylanase gene

<400> SEQUENCE: 5
ggaattccat atgaatgccc aaaccctgag t                         31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer
      sequence containing XhaI recognition sequence for
      amplifying xylanase gene

<400> SEQUENCE: 6
cccgggctcg agtcaattac aaacgacacc                           30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer
      sequence for amplifying DNA fragment encoding
      wildtype signal peptide of xylanase gene linked to
      xyd1.

<400> SEQUENCE: 7
cgggatccat gaatgcccaa accctgagt                            29

<210> SEQ ID NO 8
<211> LENGTH: 26
<212> TYPE: DNA

-continued

```
<213> ORGANISM: Artificial Sequence
<220> FEATURE:
<223> OTHER INFORMATION: Description of Artificial Sequence: Primer
      sequence for amplifying DNA fragment encoding
      wildtype signal peptide of xylanase gene linked to
      xyld1

<400> SEQUENCE: 8
cggaattctc aattacaaac gacacc                                          26
```

RECOMBINANT XYLANASE, THE PREPARATION AND USE OF THEREOF

FIELD OF THE INVENTION

The present invention relates to a novel recombinant xylanase enzyme and the use thereof, and to a process for the production of xylanase enzymes.

BACKGROUND OF THE INVENTION

Xylan is the major component of hemicellulose in plant cell wall. Xylan contains the D-xylose molecules at 1→4β linkage as backbone, as well as side chains consisting of arabinofuranose, methylglucose and acetyl at 1→3 or 1→2 linkage. There is always a great amount of xylan generated during paper manufacture. Xylan was always discharged to streams or rivers due to lack of efficient recyclization. This leads to both the loss of resource and pollution of the environment. Moreover, xylan is also abundant in feeds of livestock, whereas it is not degradable in animal digestive tract for lack of proper enzymes. Therefore, xylan degradation would merely reduce pollution through good utilization of wastes resulted from paper production, but also enhance absorption of nutrients and growth of livestock with an economic advantage owing to a decrease of required feed amount.

In view of the above circumstances, it is believed that the development of applications of microbial xylanases is the best solution. It is disclosed in such as U.S. Pat. Nos. 5,116,746, 5,179,021, 5,407,827, 5,437,992, 5,498,534 and 5,591,304 that the addition of xylanase to pulps provided an improvement in bleaching effect and degradation of residual xylan. Further, it is disclosed in such as U.S. Pat. Nos. 5,429,828, 5,445,957, 5,612,055 and 5,662,738 that the addition of xylanase to hemicellulose-rich feeds for xylan degradation provides an improvement in the absorptive efficiency of nutrients and promoted growth of animals.

Xylanase (endo-1,4-xylanase EC 3.2.1.8) is capable of degrading xylan into oligosaccharide molecules or xylose molecules. Xylanase is universal in a variety of microbes which are capable of generating energy by degrading xylan in plant cell wall through xylanase and other polysaccharide-degrading enzymes. Also, xylanase was found present in insects and crustaceans feeding on plants. It is known that this enzyme is present in living organisms except for mammals (see A., Sunna and G., Antranikian, 1997, Crit. Rev. Biothch. 17(1):39–67; Peter Biely, 1985, Trends in Biotech. 3(11):286–290).

The microbes known as being capable of producing xylanase include *Aspergillus niger*, *Aureobasidium pullulans*, Cephalosporium, *Bacillus stearothermophilus* (cf. U.S. Pat. Nos. 5,591,619, 5,534,429 and 5,491,087). However, the common disadvantages, i.e., unsatisfactory activity, low production, high expense and complicated purification procedures, were found in those prior art references. Therefore, it is still necessary to develop new xylanase enzymes and a process for the production of the enzymes without the existing problems in the prior art.

SUMMARY OF THE INVENTION

An object of the present invention is to provide a novel protein with xylanase activity and the coding nucleic acid sequence thereof.

Another object of the present invention is to provide a process for the production of a protein with xylanase activity which is characterized by high production, excellent activity and easy purification.

A further object of the present invention is to provide polymerase chain reaction (PCR) primers for cloning a protein with xylanase activity.

A still further object of the present invention is to provide novel recombinant plasmids and host cells transformed therewith according to the process of the present invention.

A still further object of the present inventions is to provide a column for catalysis of xylan in which the new protein with xylanase activity according to the present invention is immobilized.

BRIEF DESCRIPTION OF THE DRAWINGS

FIG. 3 shows the DNA sequence (841 bp) of the recombinant xylanase gene xyld1 (SEQ ID NO:1). The bold "TCA" (nucleotides 614–616) means a conjunction between the catalytic and cellulose-binding domains.

FIG. 4 shows the amino acid sequence of the recombinant xylanase gene xyld1(SEQ ID NO:2).

DETAILED DESCRIPTION OF THE INVENTION

Xylanase genes derived from microbes can be amplified by conventional techniques, such as PCR. PCR technique has been commonly utilized for amplifying particular gene since 1980's (e.g. U.S. Pat. Nos. 4,683,195, 4,683,202, etc.). The steps of PCR comprises designing and synthesis of primers containing flanking sequences of a gene fragment of interest, and then amplifying the fragment in vitro by repeating reaction cycle in a commercial automatic machine (thermal cycler). The reaction cycle consists of denaturing the double-stranded DNA, annealing with primers and synthesizing new double-stranded DNA by DNA polymerase.

In an embodiment of the present invention, a wildtype xylanase gene was obtained from *Pseudomonas fluorescens* by PCR amplification with the primers designed based on the known 5'-end and 3'-end sequences of pseudomonas xylanase gene disclosed by Millward-Sadler and Davidson [Biochem. J. 312, 39–48 (1995)]. The resultant gene fragment designated xylns was subcloned in to a plasmid.

Further, the primers utilized in the embodiment, i.e., JLF+ and JLF– were designed as follows by reference to not merely the specific sequence of *P. fluorescens* xylanase but also the consensus sequence of xylanase from other living organisms:

JLF+:
   5'-ATTACCGTTAGCGAATCAAGCTCCGGTGGCA GCAGC (SEQ ID NO:3)

JLF–:
   5'-GCCACCGGAGCTTGATTCGCTAACGGTAAT GTCGGA (SEQ ID NO:4)

Therefore, the primers are suitable for cloning xylanase genes from other living organisms.

Figure 1:
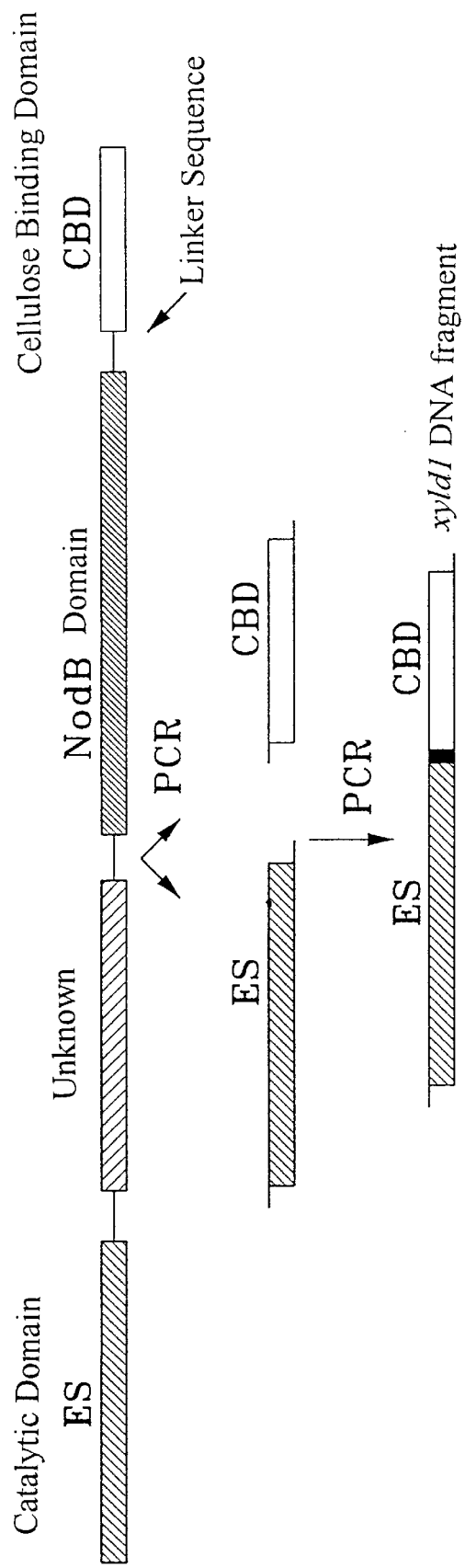
FIG. 1 shows the strategy to obtain the recombinant xylanase gene xyld1 coding sequence.
Figure 2:
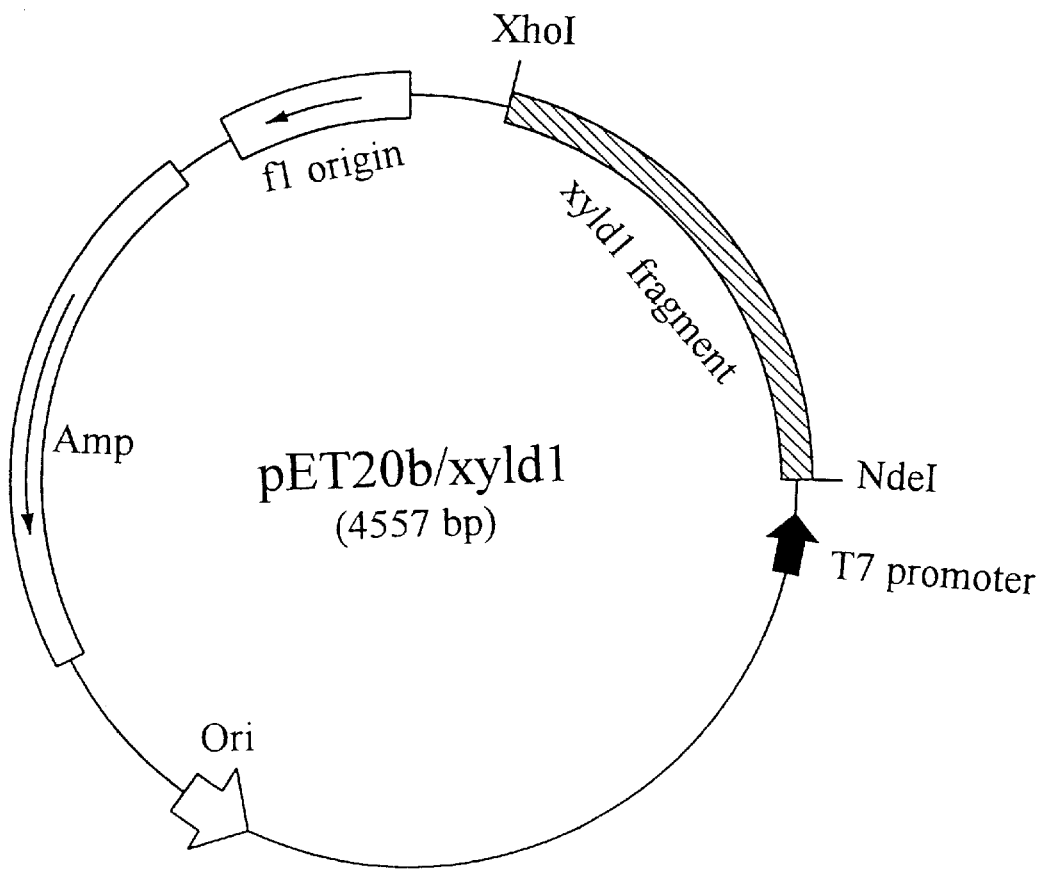
FIG. 2 shows the map of the expression vector pET20b/xyld1. Selected restriction enzyme sites are indicated.

In another embodiment of the present invention, a recombinant plasmid (see FIG. 2) containing a DNA fragment (xyld1) encoding a recombinant xylanase was obtained in PCR amplification by using overlap-extension PCR strategy (Ho et al., Gene 77, 51–59, 1989) with the plasmid containing xylns sequence as the template (see FIG. 1). The recombinant xylanase gene was designated xyld1 and merely comprises the sequences of catalytic domain (ES) and cellulose-binding domain (CBD) (see FIG. 1 and FIG. 3).

In yet another embodiment of the present invention, the DNA sequence encoding the wildtype signal peptide of *P. fluorescens* xylanase was linked to xyld1 by PCR. The resultant DNA fragment designated xylds was subcloned into an expression vector.

The amplified DNA fragments were subcloned into suitable expression vectors including vectors which are competent in bacterial yeast, mammalian and insect expression systems, such as pET-, p4X6(GPD)-, pPI9-, pBR-, pUC- or pUB-series plasmids. Practitioners will be able to choose a proper one among available expression vectors.

The expression vectors constructed according to the present invention were transformed into suitable host cells for gene expression. The suitable host cells in the present invention include bacteria (such as *Escherichia coli*), yeast (such as *Saccharomyces cerevisiae*), mammalian cells (such as mouse fibroblast cells) and insect cells (such as SF9 cell line), preferably the bacterial and yeast expression systems. However, the xylanase proteins expressed in *E. coli* are usually found in inclusion bodies. It is thus necessary to denature the inclusion bodies and dissolve xylanase therein by using urea, followed by recovering the enzymatic activity by dialysis, so that an active soluble form of xylanase is obtained.

Figure 5A:
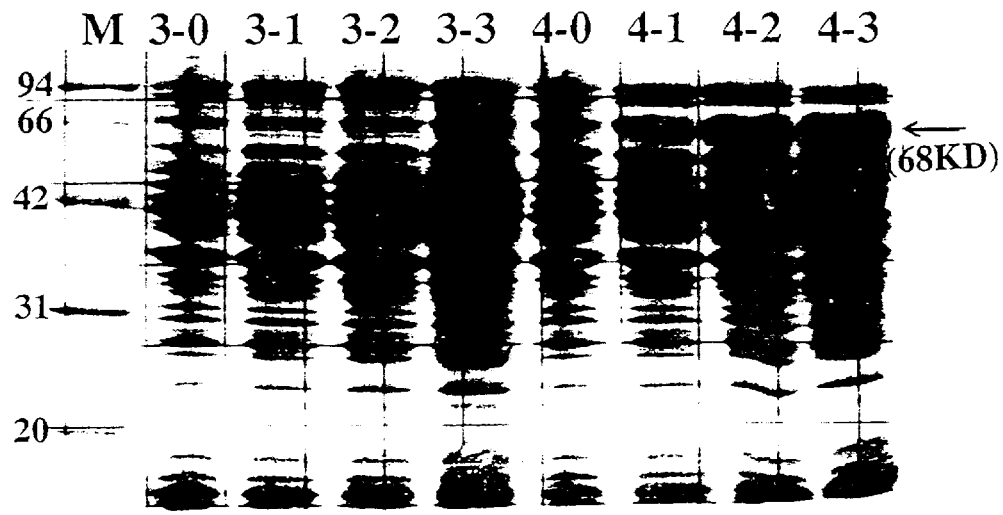
FIGS. 5A and 5B show electrophoresis analysis results (in 12% polyacrylamide gel) of the wildtype (5A) and recombinant (5B) xylanases expressed in the transformed bacteria according to the present invention; wherein in FIG. 5A, M represents a molecular weight marker; the remaining lanes represents total proteins of *E. coli* BL21 containing the expression vector pET20b/xylns; the arrow indicates the molecular weight (68 kDa) of the wildtype xylanase; and in FIG. 5B, M represents a molecular weight marker, C represents *E. coli* BL21(DE3) control (no expression of xylanase lanes 1 to 6 represent the total proteins of *E. coli* BL21(DE3) containing the expression vector pET20b/xyld1; the arrow indicates the molecular weight (34 kDa) of the recombinant xylanase according to the present invention.
Figure 5B:
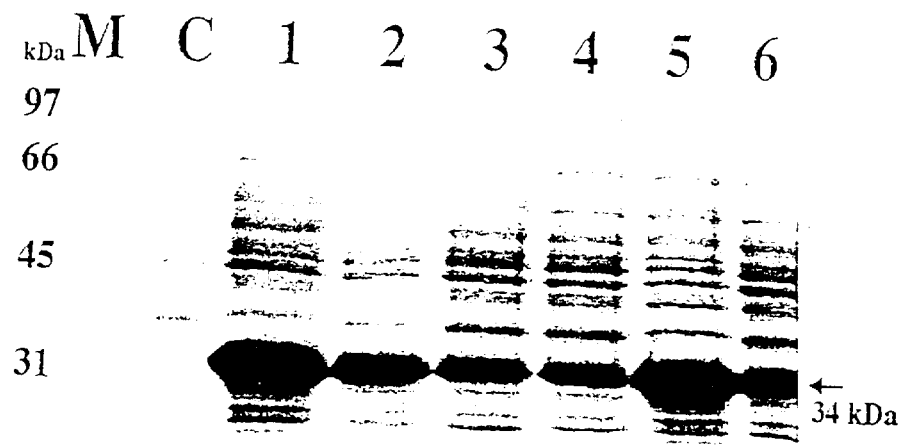
Figure 9:
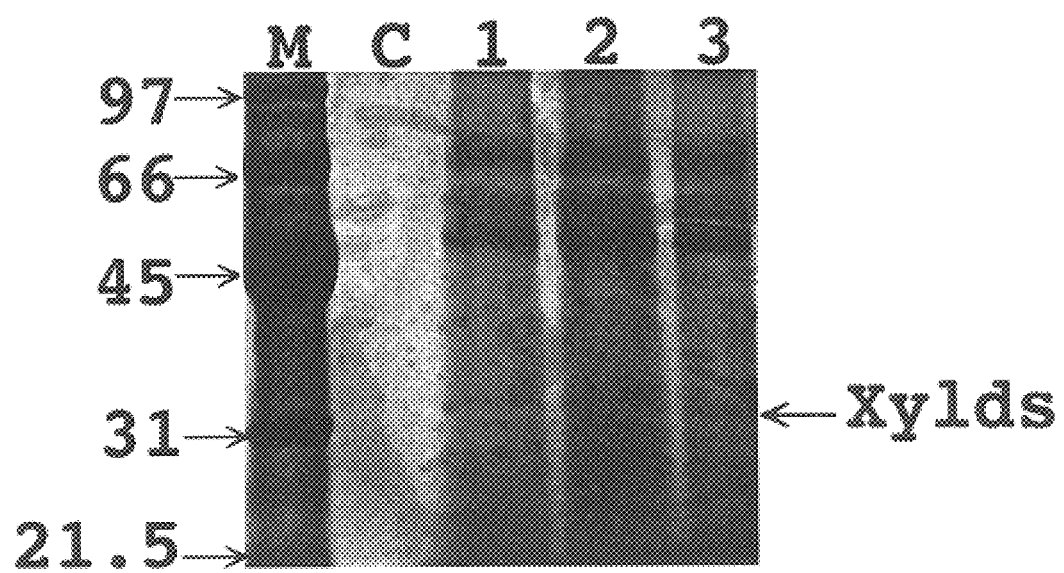
FIG. 9 shows the electrophoresis analysis in 12% polyacrylamide gel of the recombinant xylanase expressed in *Saccharomyces cereversiae* according to the present invention; wherein M represents molecular weight mark; C represents fresh medium (negative control); lane 1 represents 5× concentration of the conditioned medium; lanes 2 and 3 represent 10× concentration of the conditioned medium.

In a further embodiment of the present invention, the expression vectors containing xylns and xyld1 sequences were respectively transformed into *E. coli* for expression, followed by electrophoresis analyses of the total proteins collected from the two kinds of transformants (see FIGS. 5A and 5B). After respectively assessing the amount ratio of the Xylns or Xyld protein to the total cellular proteins of each kind of transformants, it was observed that the yield of the Xyld protein, which is partially deleted, is much greater than the yield of the wildtype protein. Also, the expression vector containing the xylds sequence was transformed into yeast for expression. A satisfactory result was obtained (see FIG. 9) when measuring the amount of the recombinant xylanase in the supernatant of the conditioned medium after culturing the transformed yeast for a relevant period.

For the expression in *E. coli*, the recombinant xylanase which was extracted from the inclusion bodies and then recovered had a good yield (about 60% of the total cellular proteins) which was 5-fold greater than that of the wildtype xylanase.

For the expression in yeast, the purification was relatively easier since the produced recombinant xylanase proteins could be secreted to the culture medium as the result of the linkage of the DNA encoding signal peptide of xylanase to xyldl. After culturing the yeast transformants at 30° C. for 36 to 38 hours, the yield was about 1 µg protein/ml medium.

In a further embodiment of the present invention, a comparison was performed among the commercial *Aureobasidium pullulans* xylanase solution (Sigma) and the enzymes Xyld, Xyln and Xylds produced by expressing xyld1, xylns and xylds, respectively. It was surprisingly found that the specific activity of those recombinant xylanases with partial deletion according to the present invention are significantly superior to either the wildtype or the commercial xylanase (see FIGS. 6 and 10).

As a result of a further comparison, the activity of the enzymes according to the present invention is 10- to 20-fold higher than the commercial *A. pullulans* xylanase and 25-fold higher than the wildtype *P. fluorescens* xylanase. Further, in light of the excellent yield of the recombinant enzymes, the present invention leads to further curtailments of expenditure so that a high industrial value in implementation is conceivable. This advantage is manifest especially in the fields of paper industry, food industry and feed industry.

Figure 7:
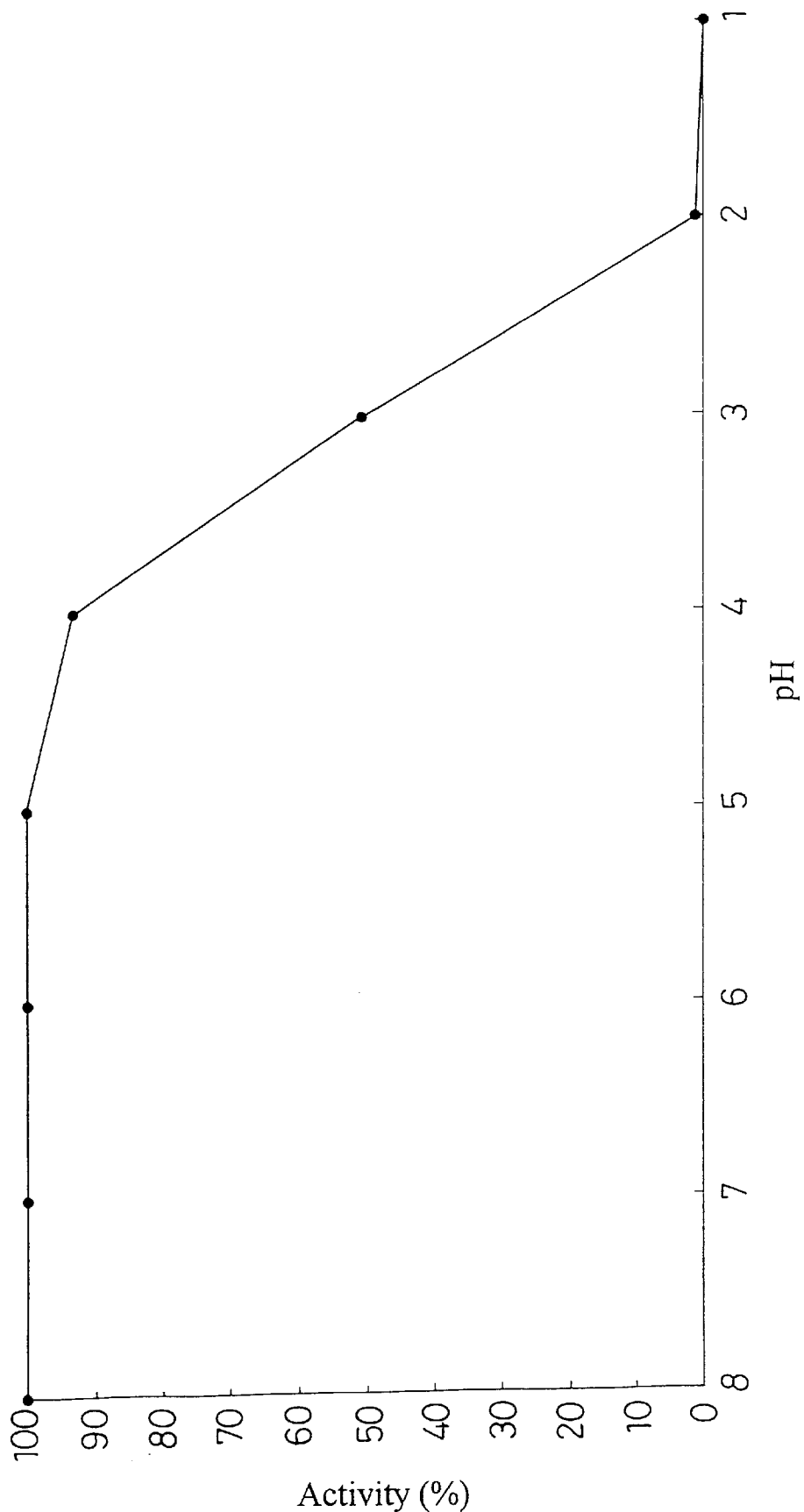
FIG. 7 shows the stability profile of Xyld to pH gradient.
Figure 8:
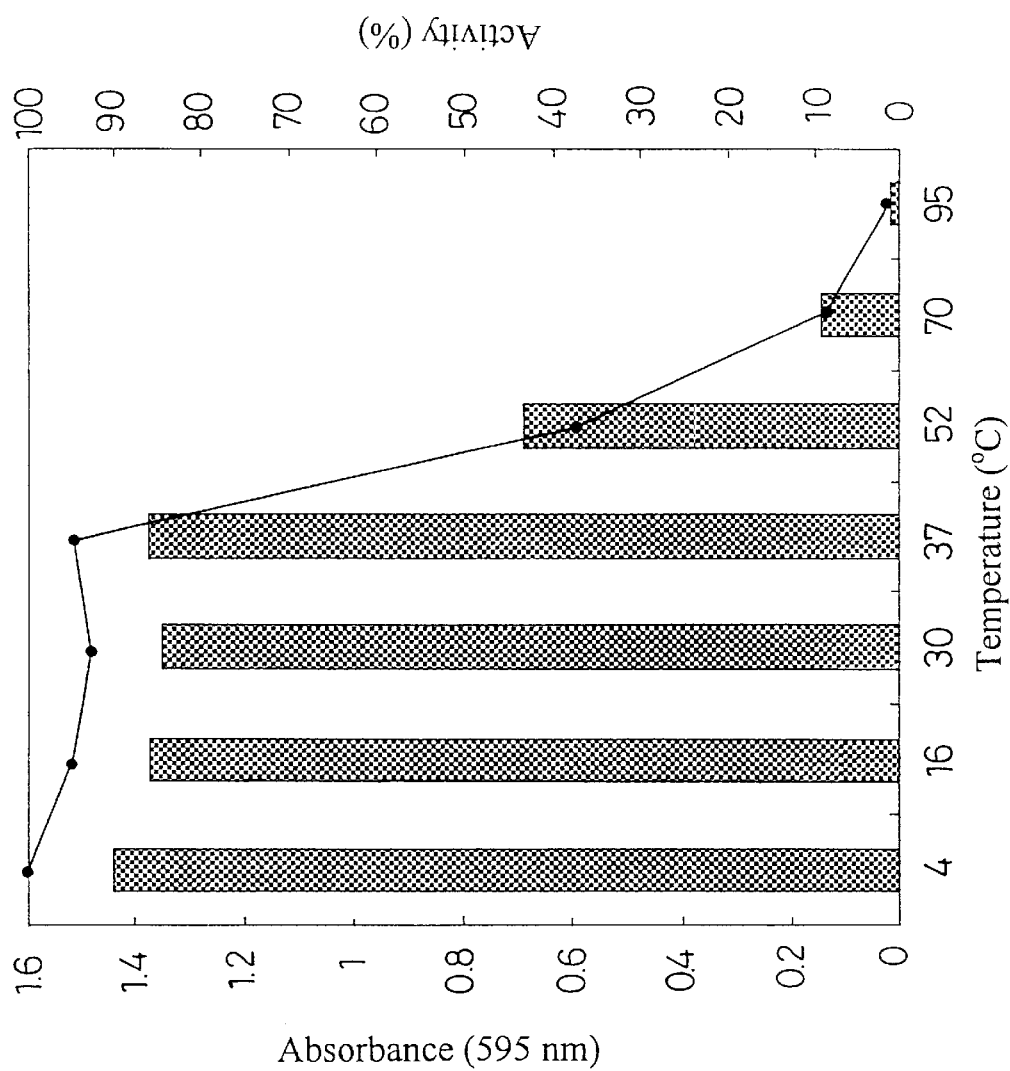
FIG. 8 shows the stability profile of Xyld in a temperature range from 4° C. to 100° C.

In a further embodiment of the present invention, the recombinant xylanases according to the present invention were subjected to activity assays at different temperatures and in various pH conditions (see FIGS. 7 and 8).

According to the above embodiments, the present invention also provides a process for producing a protein with xylanase activity by using genetically engineering technology. The process comprises the steps of:

(a) obtaining a recombinant gene by engineering a xylanase gene to lead to at least a deletion mutation;

(b) constructing an expression plasmid by operably linking the recombinant gene with a proper expression vector;

(c) transforming the expression plasmid into proper host cells;

(d) culturing the transformants in a condition allowing the expression of the xylanase gene; and (e) purifying the expressed xylanase proteins.

The process according to the present invention is not only able to produce the recombinant xylanase as embodiment hereinafter but also any proteins with xylanase activity derived from other microbes. In detail, the process according to the present invention comprises amplifying recombinant genes of interest by PCR using proper primers designed based on the consensus DNA sequence of varied xylanase genes, constructing expression vectors containing the recombinant genes and the host cells harboring the vectors, and allowing the genes expressed in the host cells to produce the proteins with xylanase activity.

chem. J., 312, pp39–48 (1995). The forward and reverse primers respectively containing an NdeI recognition sequence and a NdeI recognition sequence are listed as follows:

```
5'-GGAATTCCATATGAATGCCCAAACCCTGAGT (forward)    (SEQ ID NO:5)
         NdeI

5'-CCCGGGCTCGAGTCAATTACAAACGACACC (reverse)    (SEQ ID NO:6)
         XhoI
```

In view of the cellulose-binding capacity of the recombinant xylanase according to the present invention, it is readily contemplated by persons skilled in the art that the recombinant protein can be purified in a large scale by using columns packed with cellulose materials. In a further contemplation, xylan may be rapidly catalyzed in vitro by using columns packed with the cellulose materials to which the recombinant proteins are immobilized.

All of the literature and patents as mentioned herein are incorporated into the present invention for reference.

The following examples further illustrate the present invention, but not intended to limit the scope of the present invention.

EXAMPLE 1

Construction of the expression vector pET20b/xylns

Extraction of *Pseudomonas fluorescens* chromosomes

In a 1 liter volume of deionic water, 10 g of bacto-trypton, 5 g of bacto-yeast extracts and 10 g of NaCl were added. The solution was sterilized by autoclave and then adjusted to pH 7.5 with 1N NaOH so that a Luria-Bertani (LB) broth was obtained. A nutrition broth for bacterial culture was prepared by adding glucose to the LB broth in a final concentration 0.25%.

*P. fluorescens* (N.C.I.N.B. 10462) was inoculated into 5 ml of the nutrition broth (LB+glucose) and cultured with shaking at 37° C. for 24 hours. The culture broth was centrifuged (5,000 rpm) for 15 minutes followed by discarding the supernatant. Pellets were rinsed with deionic water and the resultant suspension was centrifuged followed by discarding the supernatant. Pellets were extracted with 0.75 ml of water and 0.75 ml of phenol for 30 minutes, followed by centrifuging (12,000 rpm) for 15 minutes. The aqueous layer (upper layer) was carfully taken out and transferred to another tube. Equal volume (0.75 ml) of phenol was added to the aqueous layer followed by repeating the above procedure of phenol extraction. The obtained aqueous layer was extracted with 0.75 ml of chloroform for 15 minutes and then subjected to centrifugation at 12,000 rpm for 15 minutes. The supernatant was transferred to another tube and a two-fold volume of ethanol was added. The suspension was centrifuged at 12,000 rpm for 15 minutes. The precipitated DNA was rinsed with 75% ethanol and taken up in a proper volume of 10 mM Tris-Cl (pH 7.5).

Amplification of the pseudomonas xylanase gene (xylns)

Two primers (forward and reverse) were synthesized according to the 5'-end (not including the sequence encoding the signal peptide) and 3'-end sequences of the xylanase gene as disclosed in Millward-Sadler and Davidson, Bio- To amplify the pseudomonas xylanase by PCR, each reaction mixture consisted of 1 μg of pseudomonas chromosomal DNA, 8 μl of 2.5 mM deoxynucleoside triphosphate mixtures (dNTPs), 10 μl of 10×Taq buffer, 1 μg each of the forward and reverse primers, 1 μl of 5U/μl Takara Taq DNA polymerase and refined water in a total volume of 100 μl. In a DNA Thermal Cycle (Perkin Elmer), the reaction mixture was heated at 94° C. for 3 minutes, followed by thirty cycles of PCR amplification conducted in a profile consisting of denaturation at 94° C. for 1 minute, primer annealing at 50° C. for 1 minute and extension at 72° C. for 1 minute, and then kept at 72° C. for 10 minutes. Aliquots of the PCR products were analyzed on a 0.8% low-melting agarose gel and visualized after ethydium bromide staining. As observed, a DNA fragment of about 1.9 kb was amplified. The piece of gel containing the amplified DNA was cut off and heated with glycogen at 65° C. to 70° C. for 15 minutes. The solution at the elevated temperature was subjected to phenol extraction and phenol/chloroform extraction as described above. Into the resultant solution 1/10 volume of 3M sodium acetate solution and 2× volume of ethanol were added, followed by storing at −70° C. for 2 hours. The DNA pellet recovered by centrifugation (12,000 rpm) was rinsed with a 70% ethanol solution and then centrifuged (12,000 rpm) again. Removing the supernatant, the DNA pellet was allowed dry and then reconstituted in refined water. The DNA fragment as purified was designated as xylns.

Construction of the expression vector pET20b/xylns

The PCR product as amplified above and the pET20b vector (Novogen, USA) were digested with restriction enzymes, NdeI and XhoI, at 37° C. for 20 hours. The digested PCR product and vector were obtained respectively by electrophoresis in a low-melting agarose gel and heating the gel as described above. The PCR product and the vector were than subjected to a ligation reaction with T4 DNA ligase at 16° C. for 2 hours. The reaction mixture was transformed into DH5α bacteria. Colonies of the transformants were enriched and subjected to plasmid DNA mini-preparation. The resultant plasmids were screened by restriction enzyme analyses to identify the ones containing the DNA inserts of the same size as xylns. The sequences of those selected DNA inserts were further determined by Sanger's protocol using Sequence Version 2.0 DNA Sequencing kit (United States Biochemical, USA).

EXAMPLE 2

Construction of the expression vector pET20b/xyld1

A pair of internal primers (JLF+ and JLF−) were designed according to the sequence of xylns and their nucleated sequences are listed as the following: (SEQ ID NO:3 and SEQ ID NO:4, respectively)

JLF+:
  5'-ATTACCGTTAGCGAATCAAGCTCCGGTGGCA GCAGC

JLF−:
  5'-GCCACCGGAGCTTGATTCGCTAACGGTAATG TCGGA

A PCR reaction was conducted as described above but using two pairs of primers (forward primer and JLF−; reverse primer and JLF+) and the plasmid pET20b/xylns as the template. Two fragments respectively encoding the catalytic domain (ES) and cellulose-binding domain (CBD) of the xylns gene were thus amplified. A further PCR reaction was conducted using the forward and reverse primers and the two fragments as templates (see FIG. 1). The electrophoresis analysis of the PCR product indicated that a fragment of about 0.83 kb was amplified in the further PCR reaction. The fragment of about 0.83 kb was purified and the sequence of the fragment was determined (see FIG. 3). The fragment and the vector pET20b (Novogen, USA) were digested with NdeI and XhoI at 37° C. for 20 hours. The digested fragment and vector were ligated and transformed into DH5α bacteria as described above. Transformants were screened and the ones containing the plasmids of interest were identified. The DNA inserts were sequenced as described above to ascertain that the expression vector pET20b/xyld1 (see FIG. 2) is constructed as expected. The plasmid pET20b/xyld1 was deposited with the Food Industry Research Development Institute (FIRDI) on Dec. 18, 1997 under the accession number CCRC 940190.

EXAMPLE 3

Construction of the expression vector p416/xylds

A DNA fragment consisting of the sequences coding for ES plus signal peptide of xylanase was amplified from purified *Pseudomonas fluorescens* chromosomal DNA by PCR using the primer JLF− and a primer corresponding to the nucleotide sequence encoding the signal peptide of xylanase gene according to the method as used in Example 1. Along the two gene fragments coding respectively for ES plus signal peptide and CBD as the templates, a further PCR amplification was conducted using another pair of primers (BamHI+ and EcoRI−, see below). As a result, a DNA fragment of 0.9 kb was amplified and designated as xylds.

```
BamHI+: 5'-CGGGATCCATGAATGCCCAAACCCTGAGT     (SEQ ID NO:7)
           BamHI

EcoRI−: 5'-CGGAATTCTCAATTACAAACGACACC        (SEQ ID NO:8)
           EcoRI
```

Figure 11:
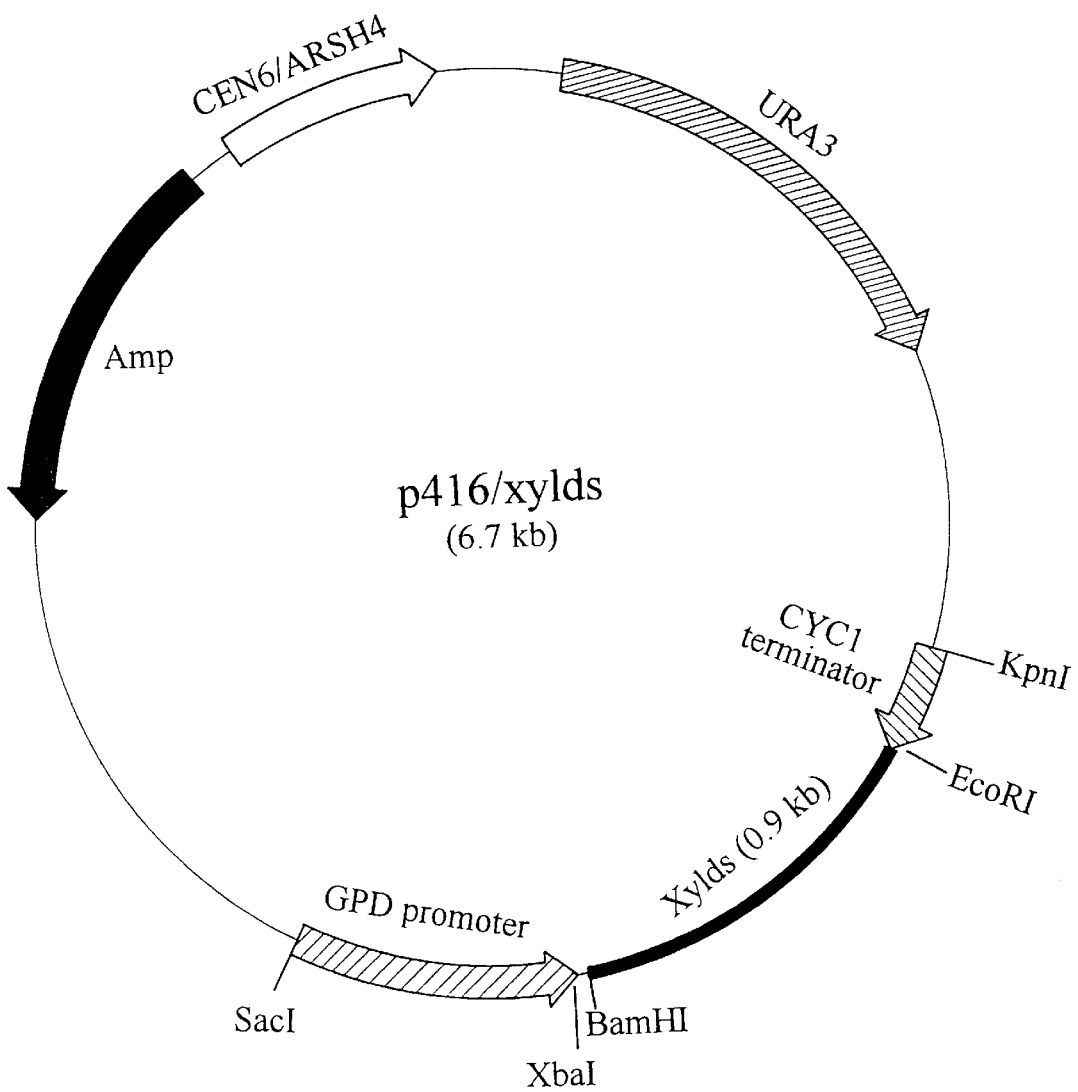
FIG. 11 is a schematic illustration of the expression plasmid p416/xylds.

The DNA fragment of 0.9 kb (xylds) was purified, digested with the restriction enzymes and ligated to the expression vector p416 according to the procedures as described in Example 1. A plasmid p416/xylds was obtained from *E. coli* DH5α bacteria transformed with the ligation mixture and identified by DNA sequencing of the DNA insert. The plasmid p416/xylds (see FIG. 11) was deposited with the Food Industry Research Development Institute (FIRDI) on Jan. 13, 1998 under the accession number CCRC 940192.

EXAMPLE 4

Expression of xylanase

The expression plasmid pET20b/xylns and pET20b/xyld1 were transformed into the competent *E. coli* BL21(DE3) cells, respectively. For each kind of transformants, bacteria were cultured in 10 ml of LB broth (ampicillin added) at 37° C. with shaking. When the optical density of the cultures measured at 600 nm wave length reached 2 ($OD_{600}=2$), the xylanase expression was induced by adding 1 mM isopropylthio-β-D-galactoside (IPTG) and then vigorously shaking at 30° C. After 3 hours, bacteria in a 1.5 ml volume of the culture broth were harvested by centrifugation. The collected bacteria were resuspended in 100 μl of 100 mM Tris-Cl buffer of pH 7.5, and then 200 μl of protein electrophoresis dye 1.5×(0.1 M dithiothretitol, 2% SDS, 0.08M Tris-Cl, pH 6.8, 15% glycerol and 0.06% bromophenol blue) were added. The mixture was heated at 95° C. for 5 minutes and centrifuged at 12,000 rpm to remove pellet. A 10 μl aliquot from the supernatant was subjected to a total protein analysis by sodium dodecylsulfate-polyarylamide (12%) gel electrophoresis (SDS-PAGE). The analysis results of the protein expression of pET20b/xylns and pET20b/xyld1 are provided FIG. 5A and 5B, respectively. As shown in FIG. 5A, the ratio of the amount of the expressed wildtype xylanase to the total bacterial proteins was about 10%. As shown in FIG. 5B, the amount of the recombinant xylanase (Xyld) as detected was almost 50% of the total cellular proteins of the transformants and the ratio was about five times the one calculated for wildtype xylanase expression. This shows a significant increase of expression of the recombinant xylanase gene according to the present invention compared to the wildtype gene.

Xylanase proteins were found to be abundant in the inclusion bodies of *E. coli* cells. Therefore, the expressed proteins with xylanase activity were obtained by solubilizing the inclusion bodies and 8M urea in the buffer consisting of 100 mM Tris-Cl and 10 mM $NaH_2PO_4$. The obtained proteins were renatured by dialysis such that urea in the proteins could be gradually removed. As a result, soluble proteins were obtained for further enzymologic analyses.

For *Saccharomyces cereversiae* expression, the plasmid p416/xylds was electroporated (2500 V, 25 μFD, 400 ohms) using Gene Pulser (Bio-Rad, USA) in to the yeast cells of BT3501 strain. The transformants were cultured with shaking in 10 ml of SD broth (0.67% YNB w/o amino acids, 2% glucose, 0.5% casamine) at 30° C. for 3 days. When the $OD_{600}$ value of the culture broth was 1.2, 1 ml of culture was transferred to a 50 ml volume of SD broth and then cultured with shaking at 30° C. until the $OD_{600}$ was 2. The cultures were centrifuged at 5000 rpm for 5 minutes. The supernatant was concentrated to one-tenth of the original volume. A 10 μl aliquot from the concentrate was dried in vacuum and then 10 μl of the electrophoresis protein dye were added. The mixture was heated at 95° C. for 5 minutes and subjected to a total protein analysis by SDS-PAGE (see FIG. 9). It was assessed that the amount of the protein of interest is about 1 μg/ml broth.

EXAMPLE 5

Determination and comparison of the activity of the recombinant xylanase

Figure 6A:
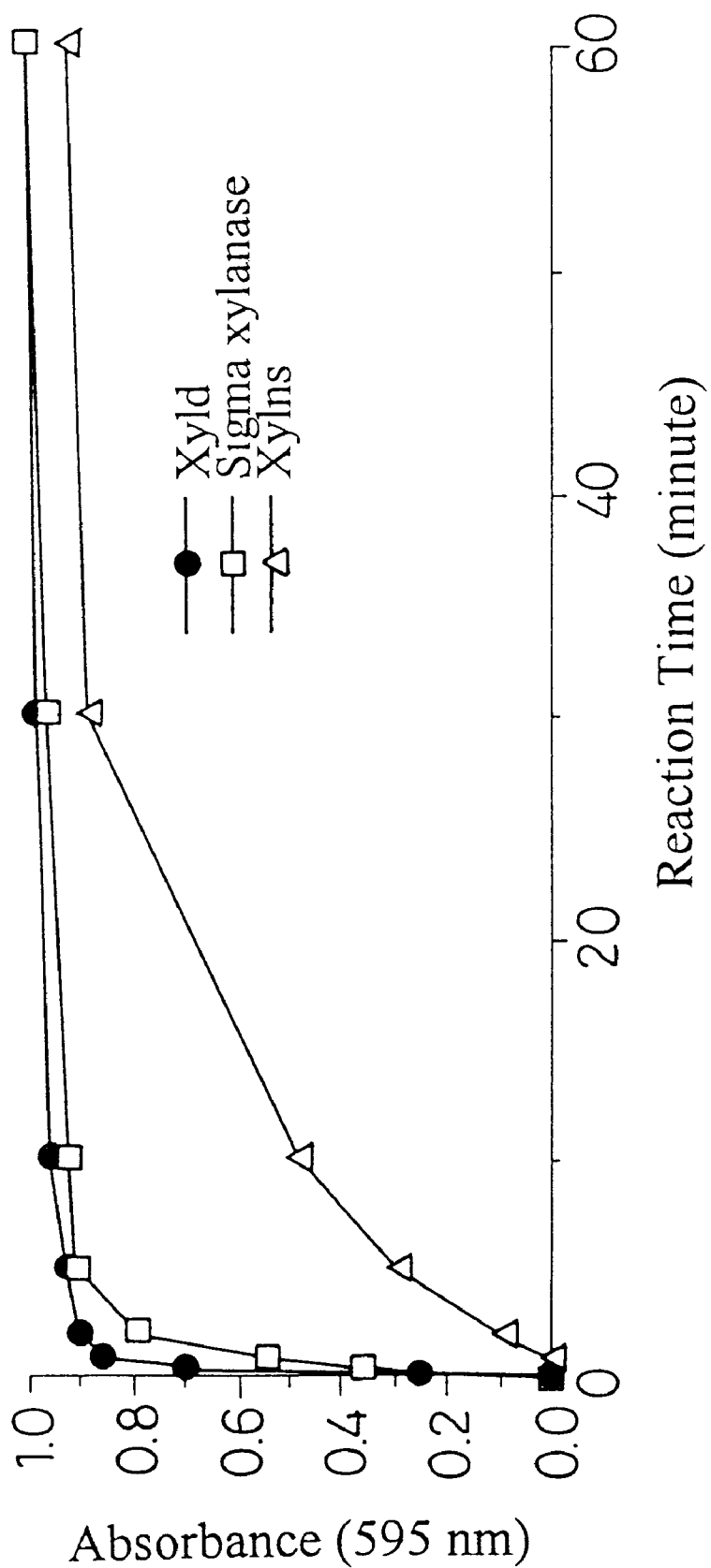
FIG. 6 shows activity comparison among Xyld (-•-), Xylns (-Δ-) and the commercial xylanase (Sigma) derived form *Aureobasidium pullulans* (-□-), where the curves in FIGS. 6A and 6B depict the differences of reaction progress curves of there the enzymes in minute and second, respectively.
Figure 6B:
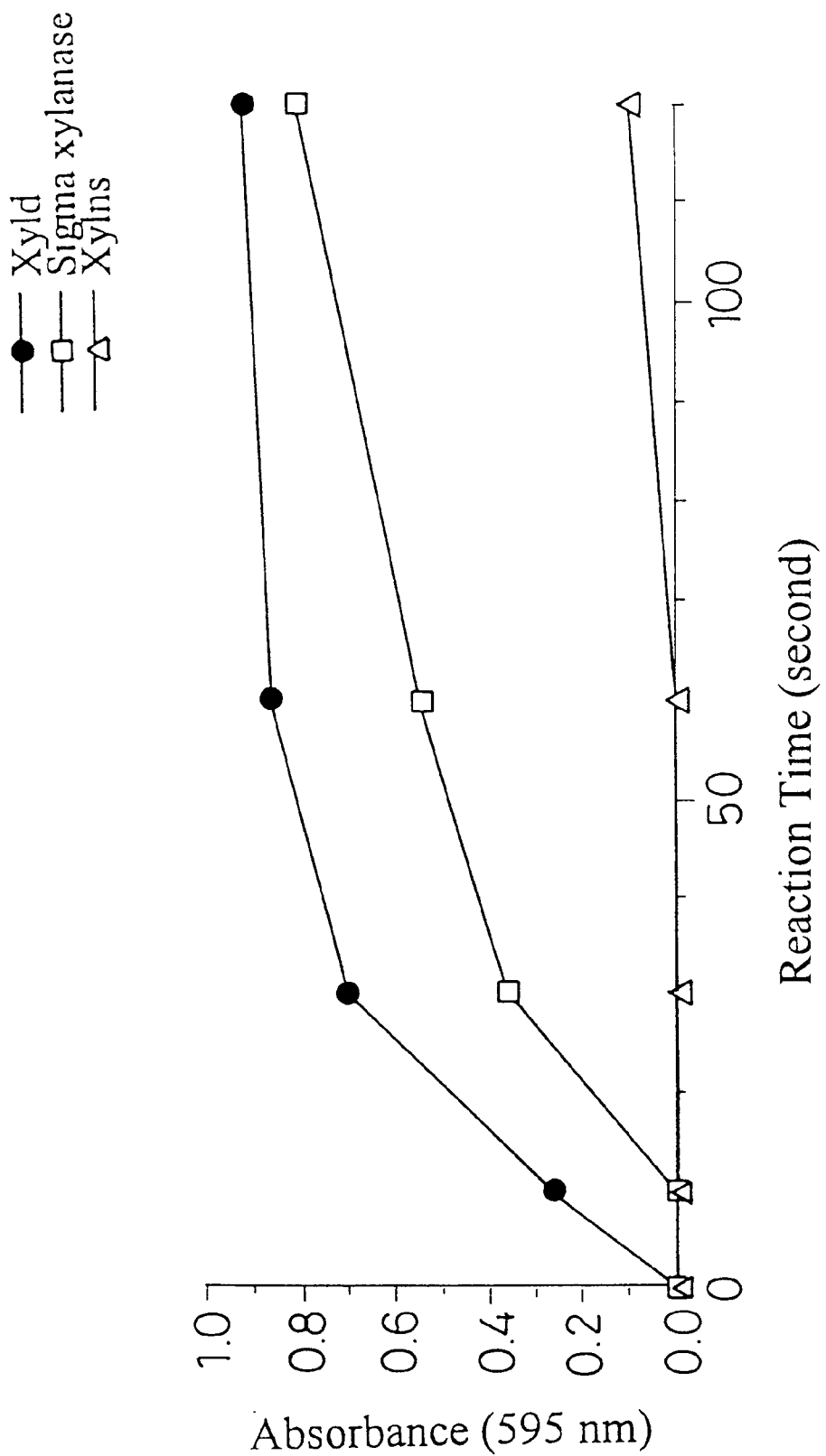
Figure 10:
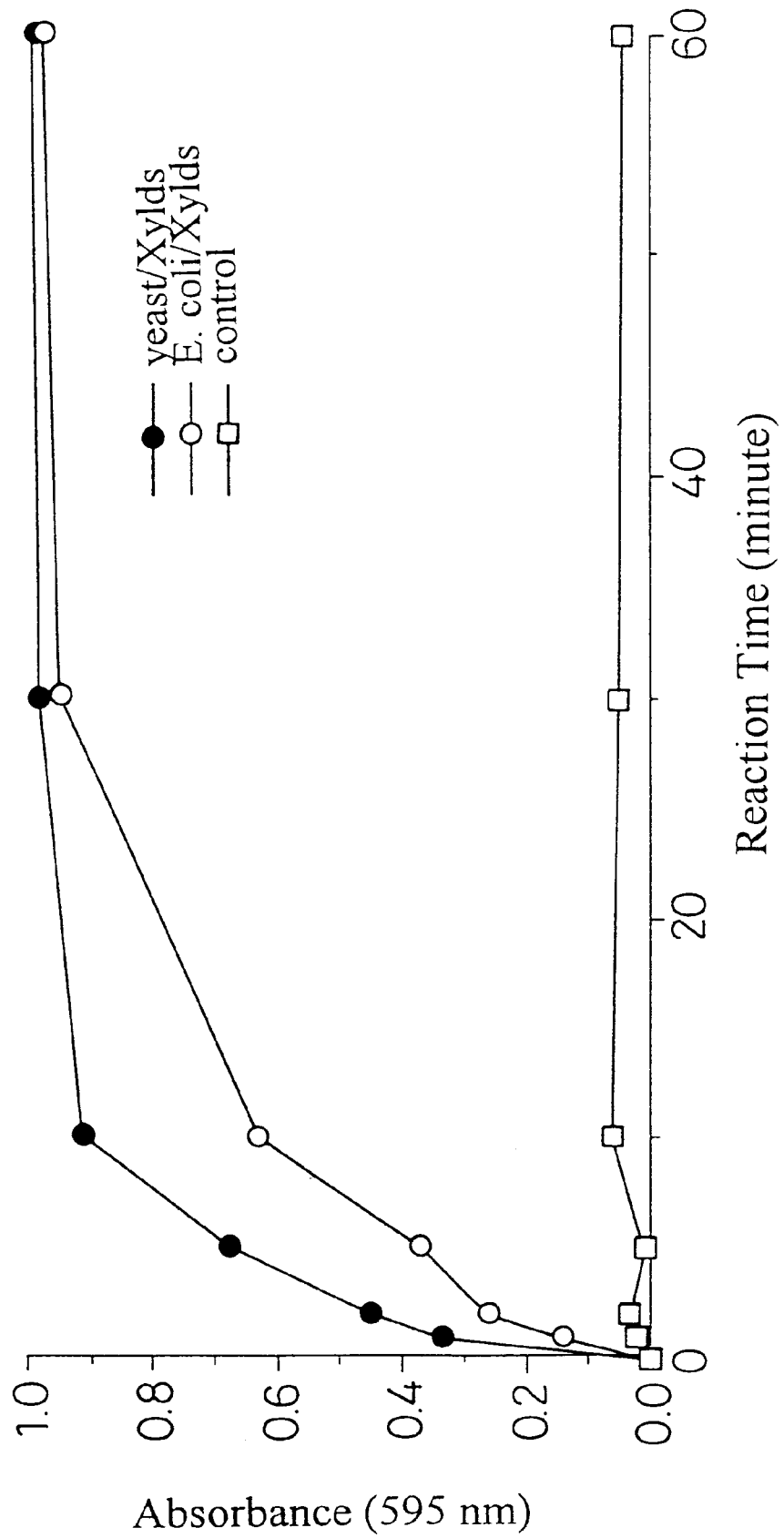
FIG. 10 shows activity comparison between the xylanase enzymes Xylds (by the expression of p416/xylds in *Saccharomyces cereversiae*) and Xyld (by the expression of pET20b/xyld1 in *E. coli*). -•-, yeast/Xylds (363.26 units/μg); -o-, *E. coli*/Xylds (123 units/μg); -□- control (the proteins in non-transformed yeast cells).

A volume (2 μl) of RBB-xylan (5 mg/ml, Sigma) solubilized in 0.05M sodium acetate buffer (pH 5.4) was placed in each tube, followed by adding 10 μl of Xyld solution, 10 μl of a commercial xylanase solution derived from *Aureobasidium pullulans* (Sigma), 100 μl of Xylns solution, and 40 μl of 10-fold concentrated yeast culture broth containing Xylds, respectively. The tubes were then incubated at 37° C. After 1, 2, 5, 10, 30, and 60 minutes, aliquot (200 μl) of each reaction mixture was transferred to another tube and mixed with a two-fold volume of 96% ethanol to cease the reaction. The tubes were placed at room temperature for 10 minutes and then centrifuged at 12,000 rpm for 5 minutes. The supernatants were subjected to spectrophotometric analysis at 595 nm. The curves of the variations of extinction with time are shown in FIGS. 6 and 10.

An activity unit (U) was defined as 1 μmole of RBB-oligoxylose or -xylose products generated per minute during enzyme digestion. The specific activities of xylanases are shown below:

| expression vector | specific activity (U/microgram) |
|---|---|
| pET20b/xylns | 5.7 |
| pET20b/xyld1 | 123 |
| p416/xylds | 363.26 |
| commercial xylanase (Sigma Chemical Co.) | 19.15 |

As shown in the above table, the activity of recombinant xylanase according to the present invention was not only superior to the wildtype enzyme, but also 6- to 20-fold higher than the commercial xylanase.

EXAMPLE 6

Stability of the recombinant xylanase to heat

Tubes each containing 20 μl of Xyld solution were incubated at 16° C., 30° C., 37° C., 52° C., 70° C. or 95° C. for 1 hour, respectively. Enzyme activities were determined as described in example 5. The activity of enzyme solution stored at 4° C. was determined as the baseline. The results showed that the optimal enzyme activity was present at the temperatures of 30° C.–37° C. The activity was not compromised at the temperatures below 52° C.

EXAMPLE 7

Determination of protein concentration

Protein concentration was assayed using dye-binding method. Aliquots (0.8 ml) were taken from the bovine serum albumin (BSA) suspensions at varied known concentrations (5 to 40 μg/ml). To each aliquot a volume 0.2 ml of protein assay dye (Bio-Rad) was added and thoroughly admixed. The absorbance at 595 nm of each mixture was determined and a standard curve of the variation of extinction with concentration was plotted. According to the same procedure, the concentration of each tested sample was able to be determined based on the standard curve.

EXAMPLE 8

Stability of the recombinant xylanase

RBB-Xylan buffers were adjusted to the pH values of 8, 7, 6, 5, 4, 3, 2 and 1, respectively. To each buffer a volume 10 μl of Xyld solution was added and incubated at 37° C. for 30 minutes. The enzymatic activities under different pH were determined. As shown in FIG. 7, the optimum enzyme activity was present at pH 5–8, whereas 50% activity of the recombinant xylanase was retained at pH=3.

Any modifications and substitutions of the above examples known to those skilled in the art are still within the scope and spirit of the present invention.

We claim:

1. An isolated nucleic acid molecule encoding a protein with xylanase activity selected from the group consisting of:
   (a) a molecule comprising the nucleotide sequence of SEQ ID NO:1; and
   (b) a molecule encoding the amino acid sequence of SEQ ID NO:2.

2. A primer selected from the sequences of SEQ ID NO:3 and SEQ ID NO:4, and the antisense sequence thereof.

3. A plasmid containing a nucleic acid molecule according to claim 1 operably linked to a vector.

4. The plasmid according to claim 3, wherein the vector is capable of expressing the nucleic acid molecule in a procaryotic cell.

5. The plasmid according to claim 4, which is pET20b/xyld1.

6. The plasmid according to claim 3, wherein the vector is capable of expressing the nucleic acid molecule in a eucaryotic cell.

7. The plasmid according to claim 6, wherein the eucaryotic cell is yeast.

8. The plasmid according to claim 6, wherein the eucaryotic cell is a mammalian cell.

9. The plasmid according to claim 6, wherein the eucaryotic cell is from an insect.

10. A transformant transformed with the plasmid according to claim 3.

11. A process for the production of a protein comprising the steps:
    (a) obtaining a recombinant gene according to claim 1, by engineering a xylanase gene to lead to at least a deletion mutation;
    (b) constructing an expression plasmid by operably linking the recombinant gene with a proper expression vector;
    (c) transforming the expression plasmid into proper host cells;
    (d) culturing the transformants in a condition allowing the expression of the xylanase gene; and
    (e) purifying the expressed xylanase proteins.

12. The process according to claim 11 wherein the recombinant gene in step (a) is encoded by the molecule according to claim 1.

* * * * *